United States Patent [19]

Nowak

[11] Patent Number: 5,304,493

[45] Date of Patent: Apr. 19, 1994

[54] METHOD FOR DETECTING A MARKER DYE IN AGED PETROLEUM DISTILLATE FUELS

[75] Inventor: Anthony V. Nowak, Fullerton, Calif.

[73] Assignee: Atlantic Richfield Company, Los Angeles, Calif.

[21] Appl. No.: 7,412

[22] Filed: Jan. 22, 1993

[51] Int. Cl.$^5$ ............................................. G01N 35/08
[52] U.S. Cl. .................................. 436/56; 436/60; 436/178; 44/312
[58] Field of Search ............... 436/56, 60, 178; 44/59

[56] References Cited

U.S. PATENT DOCUMENTS

| | | | |
|---|---|---|---|
| 3,976,572 | 8/1976 | Reick | 210/94 |
| 4,049,393 | 9/1977 | Orelup | 44/59 |
| 4,209,302 | 6/1980 | Orelup | 44/59 |
| 4,514,503 | 4/1985 | Orelup | 436/60 |
| 4,717,671 | 1/1988 | Melpolder | 436/39 |
| 4,918,020 | 4/1990 | Nowak | 436/56 |

Primary Examiner—James C. Housel
Assistant Examiner—N. Bhat
Attorney, Agent, or Firm—Michael E. Martin

[57] ABSTRACT

Aged and/or colored diesel fuels and similar petroleum distillates may be analyzed for the presence of an anthraquinone marker dye such as DuPont Chemicals Oil Blue B Liquid dye by passing a sample of the fuel through an unbonded silica solid phase extraction column which retains the color-forming agents on the column and which will provide for visual detection of the substantially nonretained marker dye in the column. A sufficiently nonpolar elution solvent such as dichloromethane or toluene may be passed through the column to elute the marker dye without removing the color-forming agents from the column. The solvent may be spectrophotometrically analyzed to detect presence of the dye.

11 Claims, No Drawings

METHOD FOR DETECTING A MARKER DYE IN AGED PETROLEUM DISTILLATE FUELS

BACKGROUND OF THE INVENTION

1. Field of the Invention

The present invention pertains to a method for detecting the presence of a color marker dye in aged or discolored diesel fuel and similar petroleum distillates.

2. Background

Petroleum distillate fuels such as regular, low-sulfur and crude diesel fuel and naval distillate fuel tend to discolor or darken, particularly with age. The formation of colored substances and darkening upon aging of these fuels masks the ability to visually detect the presence of certain marker dyes. This is particularly true if only a small amount of fuel has been dyed and then commingled with an undyed fuel.

The requirements to place visually detectable marker dyes in diesel fuels are carried out to mark or distinguish different grades of fuel and to distinguish fuels which are used for purposes which are subject to various taxes. For example, fuels sold for residential heating purposes and not subject to motor vehicle taxes are sometimes substituted for fuels which are normally subject to this tax to thereby avoid payment of the tax. Accordingly, there is a continuing and growing need to be able to detect the presence of marker dyes in diesel and similar distillate fuels to police improper use of these fuels and to meet regulatory requirements with respect to the use of different grades of fuel, particularly in motor vehicle applications.

Several inventions have been made using the concept of solid phase extraction to identify the presence of a marker dye in petroleum distillate fuels. My U.S. Pat. No. 4,918,020, issued Apr. 17, 1990, describes a solid phase extraction technique for isolating a particular commercially available marker dye in automotive gasoline. A bonded silica extraction column is provided and a sample of gasoline is passed through the column after preconditioning the column with a buffer solution. A commercially available reagent is then added to the column to form a colored complex with the marker dye which has been retained on the column.

Another solid phase extraction method is the subject of my U.S. patent application Ser. No. 07/920,071. filed Jul. 27, 1992 and assigned to the assignee of the present invention. The invention described in the above-referenced application is a method for determining the presence of DuPont Chemicals Oil Color IAR liquid marker dye in automotive gasoline by mixing a sample of the gasoline suspected of containing the dye with fine ground silica, particularly unbonded, flash chromatography grade silica to observe and compare the coloration of the silica and thereby detect the presence of the dye.

However, the use of unbonded silica as an extraction material for aged and colored petroleum distillates, such as diesel fuel, has not been contemplated heretofore since the coloring agents in such fuels are strongly polar and, it was believed, would tend to mask or prevent retention of a marker dye on the extractant material. Contrary to this belief and with the steps of the method of the present invention, it has been discovered that a visually detectable marker in colored diesel fuel can be detected even in small quantities using silica solid phase extraction columns. The advantages and a detailed description of this invention are set forth hereinbelow. A somewhat related discovery is the subject of my patent application entitled: "Detection of Marker Dyes in Aged or Dirty Motor Gasolines" filed of even date herewith.

SUMMARY OF THE INVENTION

The present invention provides a unique method for determining the presence of a color marker dye in aged and colored petroleum distillates, particularly diesel fuels.

In accordance with one important aspect of the present invention, it has been discovered that an anthraquinone dye comprising an active ingredient of 1,4-di(alkylamino) anthraquinone, in particular a petroleum fuel marker dye commercially available from DuPont Chemicals, Wilmington, Del. under the trade name "Oil Blue B Liquid" or "Blue B Liquid", may be detected in discolored, darkened or aged diesel fuel by extracting the coloring agents in a solid phase extraction column, particularly an unbonded silica column. The marker dye, being less polar than the coloring agents in the fuel, is at least partially eluted through the column and undergoes sufficient migration to provide visual detection of the presence of the dye in the fuel.

In accordance with another aspect of the invention the presence of a color marker dye comprising an active ingredient of 1,4-bis[(2-ethylhexyl/methyl/pentyl)-amino] anthraquinone, such as DuPont "Oil Blue B Liquid" and similar dyes, may be verified by extracting the fuel coloring agents in an unbonded silica extraction column followed by eluting the dye with a solvent such as toluene or dichloromethane.

Significant advantages of the method of the invention include the lack of a requirement to use or transport complex equipment into the field or transport significant quantities of chemicals or reagents. The method requires only a relatively small sample of fuel. Moreover, the invention is useful in determining the presence of the above-mentioned marker dye in relatively small concentrations as low as 5.0 ppm. A still further advantage of the method of the invention is that the fuel sample to be analyzed, if subject to marking at a lower dye concentration than 5.0 ppm, can be analyzed by simply processing a larger sample volume.

Those skilled in the art will recognize the above-described advantages and superior features of the invention together with other important aspects thereof upon reading the detailed description which follows.

DESCRIPTION OF A PREFERRED EMBODIMENT

Diesel fuels and similar petroleum distillates have a tendency to form color bodies and darken upon aging. This characteristic of such fuels makes difficult the ability to visually distinguish the presence of a visual type marker dye in the fuel sample, particularly if only a small amount of fuel with the marker dye has been commingled with a large quantity of undyed fuel. However, the ability to detect the presence of dyed fuel commingled with undyed fuel or used in applications which are in violation of regulatory requirements has been a driving force with respect to the development of methods for detecting the presence of certain visual marker dyes in such fuels. DuPont Chemicals Oil Blue B Liquid marker dye is widely used in commercial petroleum distillate fuels such as diesel and heating oils. DuPont Oil Blue B Liquid is an anthraquinone dye characterized by an active ingredient of 1,4-bis[2-ethylhexyl/methyl/pentyl)-amino] anthraquinone (59%) in xylene solvent (41%).

The use of a solid phase extraction column which would attract polar compounds known to comprise the coloring agents in distillate fuels such as diesel fuel has tended to teach away from the use of such columns as part of a method for detecting the presence of DuPont Oil Blue B Liquid marker dye and similar dyes in these fuels. However, it has been discovered that unbonded silica type solid phase extraction columns are suited to use with the method of the present invention. Color agents or bodies found in diesel fuels are polar and are very strongly held by unbonded silica columns. The DuPont Oil Blue B Liquid dye being less polar than these coloring agents or bodies is thus less strongly held on the column and will begin to elute through the column during the process of eluting the fuel sample. Sufficient migration of the marker dye may occur during the sample elution process such that it may be possible to visually positively identify the presence of the dye on a portion of the test column without further steps. Visual detection may include comparing the test column with an unused column, a neutral background or the remainder of the column material.

If identification of the dye cannot be made by eluting a sample of the fuel through an unbonded silica solid phase extraction (SPE) column, a rinse solvent may be introduced to rinse the last traces of the fuel sample from the column. The rinse solvent must be nonpolar so that it will not have any effect on the retention of the color compositions which have been extracted onto the column from the fuel sample. Heptane forms a suitable rinse solvent since it is nonpolar, has no effect on the color materials retention on the column and yet it is effective at rinsing away residual fuel sample in the column. Heptane is also less physiologically hazardous than solvents such as hexane, which is also an effective rinse solution. Moreover, heptane is also more suitable than volatile solvents such as pentane which are not particularly suited for field use.

The method of the present invention also contemplates the use of a marker dye elution solvent for removing the dye from the column to confirm its presence or to carry out further steps to verify its presence or lack thereof in the fuel sample. The choice of the marker dye elution solvent is critical. For example, polar solvents such as alcohols, acetone, esters and the like will elute the color compositions from the column. On the other hand, substantially nonpolar solvents, such as the normal alkanes will not elute the DuPont Oil Blue B Liquid dye or a similar anthraquinone dye. It has been determined that dichloromethane is an effective elution solvent although it is volatile and physiologically hazardous. Accordingly, it has been further discovered that toluene is a suitable solvent. Toluene has been determined to effectively elute the Oil Blue B Liquid dye, yet it is not as hazardous or as volatile as dichloromethane.

An example of a preferred procedure for determining the presence of an anthraquinone dye, such as DuPont Oil Blue B Liquid marker dye, and similar dyes in aged or otherwise colored petroleum distillate fuels, including diesel fuel, is set forth as follows.

EXAMPLE I

The method of the present invention is carried out, by way of example, using an unbonded silica SPE column of a type commercially available, such as from Varian Separation Products, Harbor City, Calif. under their Catalog No. 1210-2037. A 20 ml disposable plastic syringe barrel, such as a Becton Dickinson Luer-Lok is tightly fitted to the top of the silica column to act as a sample reservoir. This assembly is attached to a vacuum manifold such as Supelco, Inc. Visiprep DL disposable liner solid phase extraction vacuum manifold. A sample of discolored diesel fuel in the amount of 10.0 ml is added to the reservoir and eluted with vacuum through the silica column. It should be noted that the amount of sample utilized will depend on the total amount of dye expected to be originally present in the test sample. After the sample of suspect fuel has passed through the column, vacuum is continued to be applied to the column for at least about one minute to remove residual sample fuel material. This operation is followed by the addition of three 2.0 ml incremental doses of a rinse solvent such as heptane which are passed through the column to remove the last traces of any residual fuel sample remaining in the column.

It should be noted that, if the test is to be performed in the field where no vacuum service is available, the method of the invention can be performed manually using positive pressure, supplied by a disposable plastic syringe for example, to push the fuel sample as well as the elution solvents through the silica SPE column. For example, a 30 ml disposable plastic syringe may be operably connected to the column for performing this step.

After rinsing the above-mentioned column with heptane or a suitable rinsing solvent, 2.0 ml of toluene is added to the top of the column. The toluene is allowed to elute through the column by gravitational and adsorptive forces. If the anthraquinone dye or a similar colored marker dye is present, it will be seen emerging from the somewhat brown-colored mixture in the column as a distinct blue band. If further confirmation of the presence of the marker dye is required, the material which distinguishes itself as the blue band in the column may be completely eluted from the column with positive pressure into a spectrophotometer cell and the visible spectrum obtained. The visible spectrum of DuPont Oil Blue B Liquid anthraquinone dye dissolved in toluene is in the range of 600 to 700 nanometers. Two distinct absorption maxima are observed at 600 and 650 nanometers, respectively, which are characteristic of the DuPont Oil Blue B Liquid dye and can thus be used for identification purposes. The visible spectrum of toluene may be obtained by taking a 10.0 ml sample of No. 2 crude diesel through the spectrophotometer procedure. If DuPont Oil Blue B Liquid dye is present, the characteristic absorption maxima of the photometer at 600 nm and 650 nm will be easily detected confirming presence of the dye.

Although a preferred embodiment of the present invention has been described hereinabove, those skilled in the art will recognize that various substitutions and modifications may be made to the inventive method without departing from the scope and spirit of the appended claims.

What is claimed is:

1. A method for determining the presence of an anthraquinone marker dye in petroleum distillate fuels, including diesel fuel and naval distillate fuel, said method comprising the steps of:

passing a sample of fuel suspected of containing said marker dye through a solid phase extraction column containing unbonded silica; and determining a change in color said column to detect the presence of said marker dye by comparing said column with one of an unused test column containing unbonded silica, a neutral background and uncolored material in said column.

2. The method set forth in claim 1 including the step of:
adding a nonpolar dye elution solvent to said column to elute said marker dye from said column and determining the presence of said marker dye in said dye elution solvent.

3. The method set forth in claim 2 including the step of:
rinsing residual fuel sample from said column prior to introducing said dye elution solvent to said column.

4. The method set forth in claim 3 wherein:
the step of rinsing said column is carried out with one of hexane and heptane.

5. The method set forth in claim 3 wherein:
the step of eluting said marker dye with said dye elution solvent is carried out with one of dichloromethane and toluene.

6. The method of claim 1, wherein:
said marker dye includes an active ingredient of 1,4-bis[(2-ethylhexyl/methyl/pentyl)-amino] anthraquinone.

7. A method for determining the presence of an anthraquinone marker dye in aged or colored diesel fuel comprising the steps of:
providing an unbonded silica solid phase extraction column and passing a sample of fuel suspected of containing said marker dye through said column while comparing a portion of said column with one of an unused test column containing unbonded silica, a neutral background and uncolored material in said column for a change in color indicating the presence of said marker dye;
passing a nonpolar dye elution solvent comprising one of dichloromethane and toluene through said column to elute said marker dye; and
comparing a portion of said column with one of an unused test column containing unbonded silica, a neutral background and uncolored material in said column to detect a change in color indicating the presence of said marker dye.

8. The method set forth in claim 7 including the step of:
rinsing residual fuel sample from said column with a rinsing solvent prior to passing said dye elution solvent through said column.

9. The method set forth in claim 8 including the step of:
providing said rinsing solvent as at least one of hexane and heptane.

10. The method set forth in claim 7 including the step of:
providing spectrophotometric analysis of a quantity of said dye elution solvent after passing said dye elution solvent through said column to determine the presence of said marker dye in said dye elution solvent.

11. The method set forth in claim 7 wherein:
said marker dye includes an active ingredient of 1,4-bis[(2-ethylhexyl/methyl/pentyl)-amino] anthraquinone.

* * * * *